(12) United States Patent
Pruitt et al.

(10) Patent No.: US 8,449,525 B2
(45) Date of Patent: May 28, 2013

(54) DIALYSIS CATHETER ASSEMBLY

(75) Inventors: Sean Pruitt, Franklin, MA (US); Lee C. Burnes, Franklin, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/165,097

(22) Filed: Jun. 21, 2011

(65) Prior Publication Data

US 2012/0330231 A1    Dec. 27, 2012

(51) Int. Cl.
*A61M 25/10* (2006.01)

(52) U.S. Cl.
USPC .................................. 604/509; 604/103.02

(58) Field of Classification Search
USPC ............................................. 604/509, 103.02
See application file for complete search history.

(56) References Cited

U.S. PATENT DOCUMENTS

| | | | |
|---|---|---|---|
| 4,932,944 A * | 6/1990 | Jagger et al. | 604/191 |
| 5,114,423 A | 5/1992 | Kasprzyk et al. | |
| 5,496,311 A | 3/1996 | Abele et al. | |
| 5,509,897 A | 4/1996 | Twardowski et al. | |
| 5,766,151 A | 6/1998 | Valley et al. | |
| 5,807,329 A * | 9/1998 | Gelman | 604/102.03 |
| 6,132,824 A | 10/2000 | Hamlin | |
| 7,309,324 B2 | 12/2007 | Hayes et al. | |
| 7,419,696 B2 | 9/2008 | Berg et al. | |
| 7,468,027 B2 | 12/2008 | Barbut et al. | |
| 7,491,188 B2 | 2/2009 | Holman et al. | |
| 7,754,238 B2 | 7/2010 | Iversen et al. | |
| 2003/0181975 A1 | 9/2003 | Ishii et al. | |
| 2007/0225800 A1 * | 9/2007 | Sahatjian et al. | 623/1.42 |
| 2007/0287956 A1 * | 12/2007 | Tal | 604/96.01 |
| 2009/0130021 A1 | 5/2009 | Munch et al. | |
| 2010/0015200 A1 | 1/2010 | Mcclain et al. | |
| 2011/0092876 A1 * | 4/2011 | Bailey | 604/6.16 |

* cited by examiner

Primary Examiner — Aarti B Berdichevsky
(74) Attorney, Agent, or Firm — John Paul Mello, Esq.

(57) ABSTRACT

A catheter assembly includes an elongated main body defining two or more longitudinal lumens including distally positioned openings. One or more side-ports are defined in the main body communicating with at least one of the two or more longitudinal lumens. The catheter assembly also includes an inflatable balloon disposed around a portion of the main body. The inflatable balloon includes a distal end disposed substantially adjacent to a proximal side of one or more side-ports. The inflatable balloon in the inflated state is adapted to extend at partially over the one or more side-ports.

16 Claims, 6 Drawing Sheets

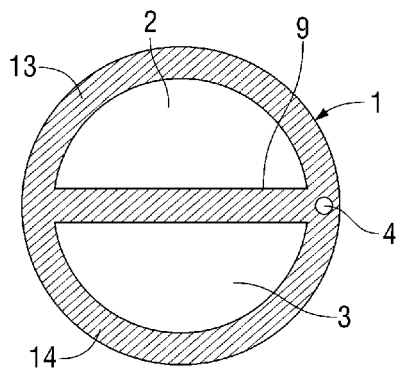
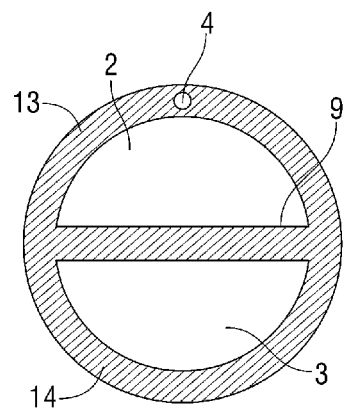
FIG. 3          FIG. 4
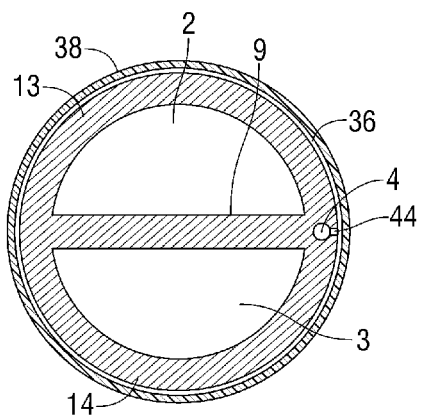
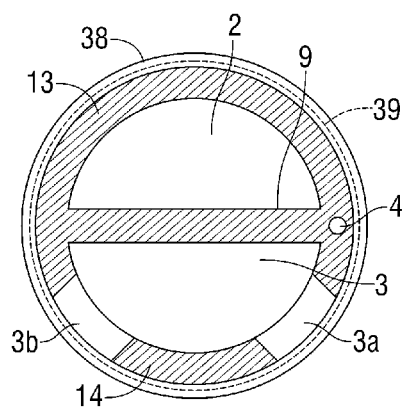
FIG. 5          FIG. 6

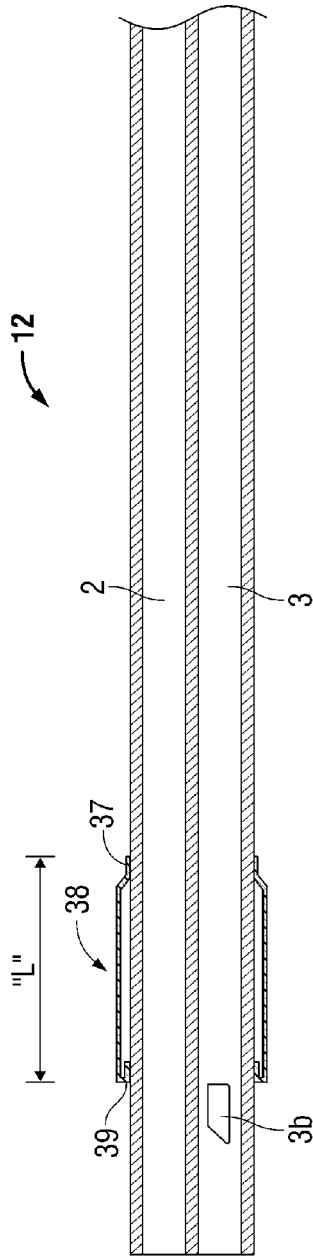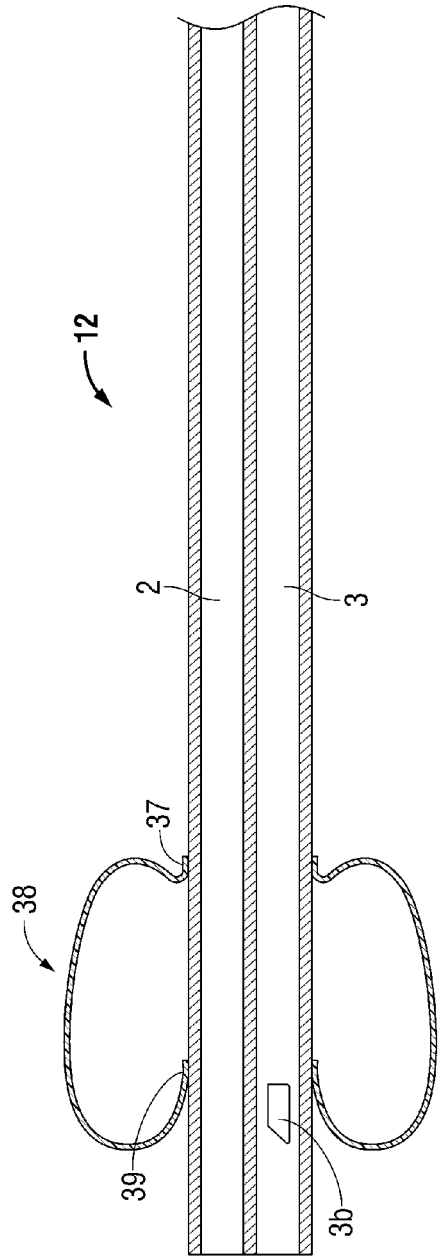

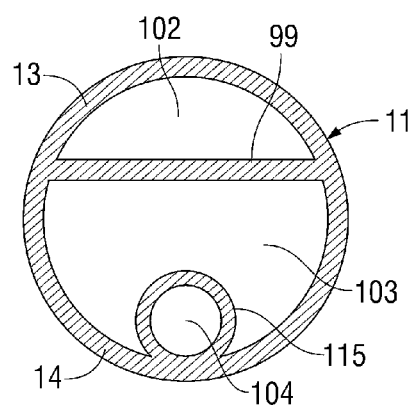
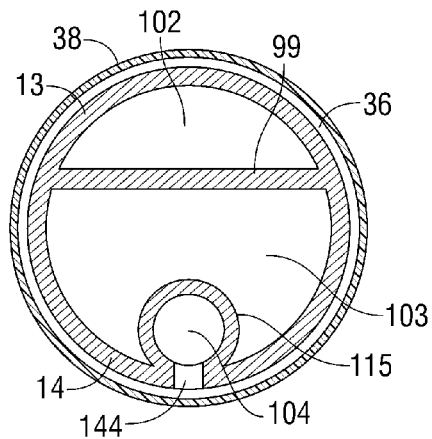
FIG. 9  FIG. 10
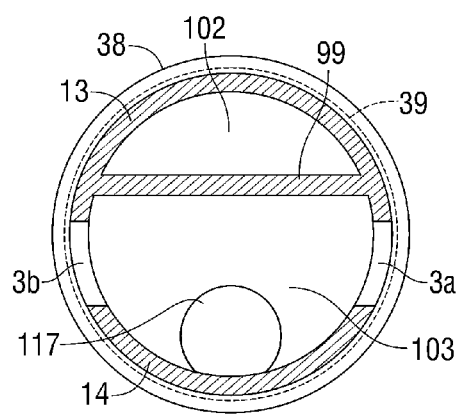
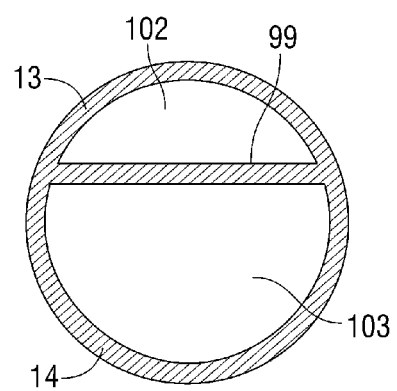
FIG. 11  FIG. 12

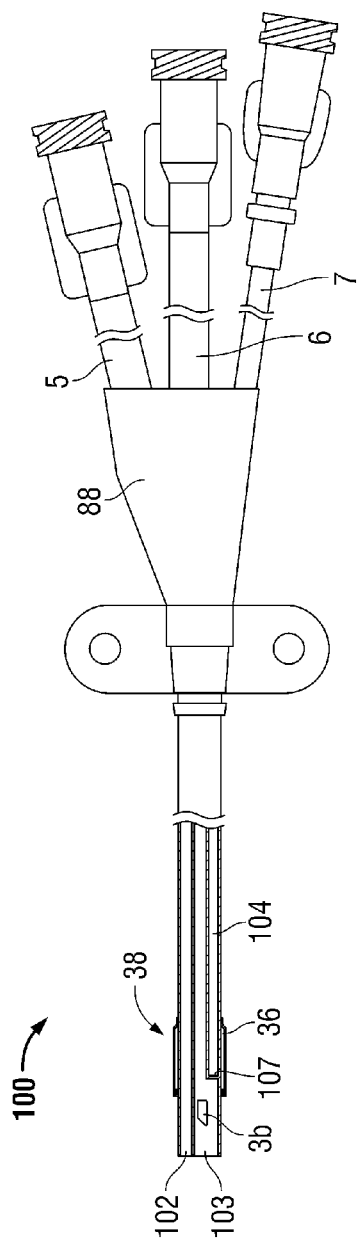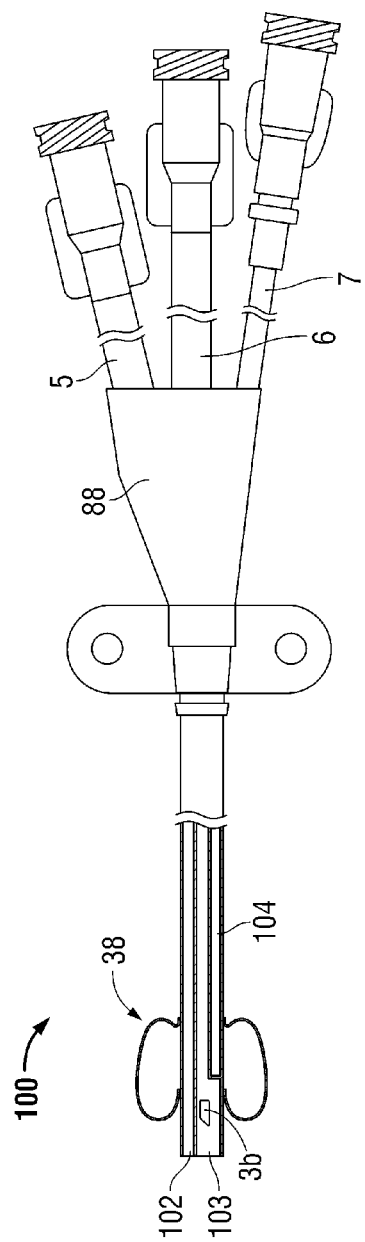

DIALYSIS CATHETER ASSEMBLY

BACKGROUND

1. Technical Field

The present disclosure relates to catheters for use in medical applications and, more particularly, to a dialysis catheter assembly including an inflatable balloon.

2. Discussion of Related Art

Catheters are flexible medical instruments for use in the withdrawal and introduction of fluids to and from body cavities, ducts, and vessels. Catheters have particular application in hemodialysis procedures, in which blood is withdrawn from a blood vessel for treatment and subsequently returned to the blood vessel for circulation through a patient's body. The use of long-term chronic catheters in the treatment of patients requiring dialysis is common due to the necessity of repeated dialysis treatments.

Hemodialysis catheters with multiple lumens typically permit bi-directional fluid flow within the catheter, whereby one lumen is dedicated to the withdrawal of fluid from a vessel, and at least one other lumen is dedicated to the return of fluid to the vessel. Generally, the lumen through which fluid is withdrawn is referred to as the "aspiration" lumen, and the lumen through which fluid is returned is referred to as the "perfusion" lumen. Triple-lumen catheters may also enable the passage of other fluids including medicants in addition to the general use of dialysis. Some multiple-lumen catheters may include a side-port formed in a wall portion of the catheter.

In a hemodialysis procedure, after placement of a multiple-lumen catheter in a patient, blood is withdrawn from the patient through the aspiration lumen of the catheter and/or the side-port associated with the aspiration lumen, and is directed to a hemodialysis unit. The dialyzed blood is then returned to the patient's circulation through the perfusion lumen of the catheter and/or any side-port associated with the perfusion lumen.

Various tissue may begin to adhere to the exterior surface of the catheter after a period of time. These various tissues may impede the performance of the dialysis catheter by disrupting the flow of blood around the catheter or blocking the side-ports or distal opening in the lumens. For example, central vein stenosis and occlusion is commonly associated with placement of peripherally-inserted central venous catheters. More specifically, the trauma and inflammation related to catheter placement, such as denudation of the endothelium of the vessel surrounding the catheter, may result in microthrombi formation, intimal hyperplasia and fibrotic response which, over time, narrows the vessel significantly and can close off blood flow around the dialysis catheter. Similarly, thrombus or fibrin sheath may begin to adhere to the exterior of the catheter and eventually obscure any side-ports or distal openings.

Central vein stenosis, thrombus, and fibrin sheath adhesion around the catheter may result in flow disturbance or obstruction of the catheter ports and may affect the delivery of dialysis. Such flow disruption or obstruction diminishes the useful life of the catheter and may require more frequent removal and replacement of the catheter to restore flow. Improved catheter devices are needed to minimize the occurrence of central vein stenosis, thrombus or fibrin sheath adhesion to avoid hemodialysis access failure and other complications.

SUMMARY

The present invention provides a catheter having a inflatable balloon on a portion of an outer surface thereof configured to dislodge various tissue that may adhere to the surface of the catheter or push against the catheter from the vessel in which the catheter resides.

In general, in one aspect, the implementation of the disclosure features, a catheter assembly including an elongated main body defining at least two longitudinal lumens including distally positioned openings. At least one side-port defined in the main body communicates with at least one of the longitudinal lumens. An inflatable balloon is disposed around a portion of the main body and includes a distal end disposed substantially adjacent to a proximal side of the at least one side-port. The inflatable balloon in an inflated state is configured to extend at partially over the at least one side-port.

One or more of the following features may also be included. The elongated main body may also define a third lumen configured to facilitate fluid flow to the inflatable balloon. The third lumen is integrated in a wall of the elongated main body.

The catheter assembly may include a chamber defined between the inflatable balloon and the elongated main body. The main body defines an inflation-port disposed and configured to place the third lumen in fluid communication with the chamber.

The inflatable balloon may be configured for delivery of an anti-restenotic and or anti-thrombogenic agent to an area of a vessel surrounding the catheter assembly.

In general, in another aspect, the implementation of the disclosure may feature a multiple-lumen catheter assembly including an elongated main body defining a longitudinal axis and an internal septum extending the length thereof. The main body and the septum define at least two internal lumens extending longitudinally along the longitudinal axis, wherein the first and second lumens occupy at least a portion of a traverse cross-section of the main body. The elongated main body also includes at least one side-port in fluid communication with the internal lumens. An inflatable balloon is disposed around a portion of the elongated main body which includes a distal end disposed substantially adjacent to the at least one side-port. A third lumen is disposed in fluid communication with the inflatable balloon.

One or more of the following features may also be included. The third lumen is disposed within one of the first and second lumens. In other embodiments, the third lumen is integrated in a wall of the main body. The elongated main body defines an inflation port disposed and configured to place the third lumen in fluid communication with a chamber defined between the inflation balloon and the elongated main body. The inflation lumen may be provided with an end cap adapted to fluidly seal a distal end of the inflation lumen The inflatable balloon may be configured for delivery of an anti-restenotic or anti-thrombogenic agent to an area of a vessel surrounding the multiple-lumen catheter assembly.

In general, in another aspect, the implementation of the disclosure may feature a method of dislodging tissue from a catheter including providing a dialysis catheter having an elongated main body defining a longitudinal axis and having a length along the longitudinal axis between a distal end and a proximal end. The elongated main body further includes at least one internal lumen. An inflatable balloon is disposed on an outer surface of the elongated main body and is configured to move from a deflated state to an inflated state. The inflatable balloon is inflated to dislodge tissue from the elongated main body.

One or more of the following features may also be included. The catheter also includes a side-port in fluid communication with the internal lumen. The inflatable balloon is disposed adjacent to the side-port and may be configured to extend at least partially over the side-port when in the inflated state. The inflatable balloon may be disposed adjacent the distal end of the elongated main body The method may also include deflating the inflatable balloon and then flowing fluid through the internal lumen and out the side-port to remove any tissue dislodged by the inflatable balloon and pushed into the side-port.

The inflatable balloon may be a drug eluting balloon. The drugs eluted by the inflatable balloon may include anti-restenotic agents or anti-thrombogenic agents.

BRIEF DESCRIPTION OF THE DRAWINGS

Objects and features of the presently-disclosed dialysis catheter assembly will become apparent to those of ordinary skill in the art when descriptions of various embodiments thereof are read with reference to the accompanying drawings, of which:

FIG. 3 is an enlarged, cross-sectional view taken along line 3-3 of FIG. 1;

FIG. 4 is an enlarged, cross-sectional view similar to FIG. 3, showing another embodiment of the catheter main body;

FIG. 5 is an enlarged, cross-sectional view taken along line 5-5 of FIG. 1;

FIG. 6 is an enlarged, cross-sectional view taken along line 6-6 of FIG. 1;

FIGS. 7 and 8 are enlarged, longitudinal cross-sectional views of the area of detail indicated in FIG. 1 illustrating a distal portion of the catheter assembly, including the inflatable balloon, during different stages of operation of the inflatable balloon;

FIG. 9 is an enlarged, cross-sectional view taken along line 9-9 of FIG. 2;

FIG. 10 is an enlarged, cross-sectional view taken along line 10-10 of FIG. 2;

FIG. 11 is an enlarged, cross-sectional view taken along line 11-11 of FIG. 2;

FIG. 12 is an enlarged, cross-sectional view taken along line 12-12 of FIG. 2;

FIGS. 15 and 16 are top, partial, cross-sectional views of the catheter assembly of FIG. 2, including the inflatable balloon, during different stages of operation of the inflatable balloon.

DETAILED DESCRIPTION

Figure 1:
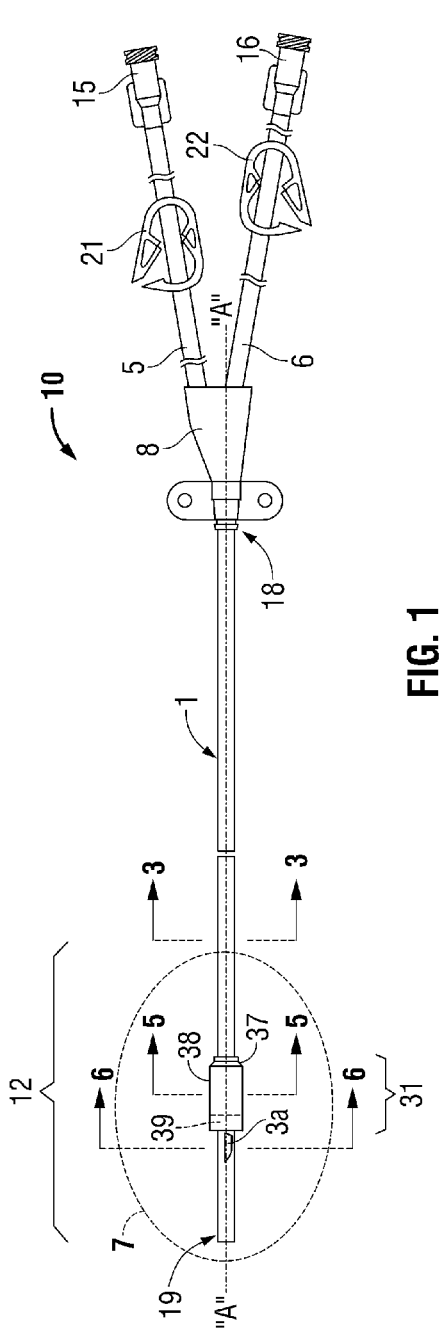
FIG. 1 is a top view of an embodiment of a catheter assembly including an inflatable balloon in accordance with the present disclosure.

Hereinafter, embodiments of the presently-disclosed dialysis catheter assembly are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, that is closer to a user, such as a clinician or nurse, and the term "distal" refers to that portion of the device, or component thereof, farther from the user.

As it is used in this description, the term "patient" generally refers to a human patient or other animal, and the term "clinician" generally refers to a doctor, nurse or other care provider and may include support personnel.

The presently-disclosed catheter assembly embodiments may be applicable to a variety of catheter-related procedures, such as, for example, hemodialysis, cardiac, abdominal, urinary, and intestinal procedures, in chronic and acute applications.

Turning now to the drawings and referring first to FIGS. 1, 3 and 5 through 8, there is shown a catheter assembly 10 in accordance with an embodiment of the present disclosure. Catheter assembly 10 includes an elongated catheter main body 1 and an inflatable balloon 38 disposed around a portion 31 of the catheter main body 1. Catheter main body 1 may be made of a synthetic resin, such as polyurethane, or other material. In some embodiments, the catheter main body 1 is formed of a soft elastic material, such as silicone, which may require thicker walls because of the pliability of the silicone. Silicone may be preferred for certain applications because it is inert. Catheter main body 1 may include an internal septum 9 (FIG. 3) extending longitudinally along a longitudinal axis "A-A" defined by the catheter main body 1. Catheter main body 1 may be formed with three lumens extending longitudinally along the longitudinal axis "A-A", namely, a perfusion lumen 2 to facilitate fluid flow in a first direction, an aspiration lumen 3 to facilitate fluid flow in a second direction (e.g., opposite to the first direction), and an inflation lumen 4 to facilitate fluid flow into, and out of, the inflatable balloon 38.

Generally, the septum 9 and the walls of the catheter main body 1 form the perfusion lumen 2 and the aspiration lumen 3. More specifically, as shown in FIG. 3, the perfusion lumen 2 is defined by the perfusion-lumen wall portion 13 and the septum 9, and the aspiration lumen 3 is defined by the aspiration-lumen wall portion 14 and the septum 9. Although the septum 9 is in the form of a flat strip, which divides the generally hollow catheter main body 1 into two substantially semi-cylindrical lumens, the septum 9 may be formed in various other configurations, such as a Y-shape forming three lumens.

In some embodiments, the perfusion lumen 2 and the aspiration lumen 3 are generally D-shaped in traverse cross-section (i.e., cross-section traverse to the longitudinal axis "A-A") and have substantially equal cross-sectional areas. In other embodiments, the aspiration lumen (e.g., 103 shown in FIG. 9) may have a larger cross-sectional area than the cross-sectional area of the perfusion lumen (e.g., 102 shown in FIG. 9). The perfusion lumen 2 and the aspiration lumen 3 may terminate at openings at the distal end of the catheter main body 1. Catheter assembly 10 may include one or more side-ports, such as side-ports 3a, 3b shown in FIG. 6, defined in the aspiration-lumen wall portion 14 and/or one or more side-ports (not shown) defined in the perfusion-lumen wall portion 13. In an alternative embodiment not shown, a dialysis catheter known to be reversible, such as the PALINDROME™ or the MAHURKAR® Maxid™ catheters, may include a side-port such as shown in FIG. 6 in the catheter main body 1 in both the aspiration-lumen wall portion 14 and the perfusion-lumen wall portion 13.

Inflation lumen 4 (FIG. 3) may have a relatively small cross-section traverse to the longitudinal axis "A-A", as compared to the traverse cross-section of the perfusion lumen 2 and the aspiration lumen 3. Inflation lumen 4 may be integrally formed in the walls of the catheter main body 1, and may be disposed at the junction of the perfusion-lumen wall portion 13 and the aspiration-lumen wall portion 14. Inflation lumen 4 or portion thereof may additionally, or alternatively, be disposed within the septum 9. The shape, size and location of the inflation lumen 4 may be varied from the configuration shown in FIG. 3 without departing from the scope of the invention.

FIG. 4 illustrates an embodiment of the catheter main body 1 in which the inflation lumen 4 is disposed in the perfusion-lumen wall portion 13. In some embodiments, such as shown in FIG. 9, the inflation lumen 104 may be disposed within one of the two or more lumens 103 defined by the catheter main body.

To facilitate connection of the catheter assembly 10 to a medical device, e.g., a dialyzer, an injection syringe, or other extracorporeal apparatus, a catheter hub 8 of the catheter assembly 10 is provided with extension tubes 5 and 6. Catheter main body 1 includes a proximal end 18 and a distal end 19. The proximal end 18 is coupled to the catheter hub 8, whereby the perfusion lumen 2 is fluidly coupled to the extension tube 5 and the aspiration lumen 3 is fluidly coupled to the extension tube 6. Extension tubes 5 and 6 may be made of flexible synthetic resin, such as silicone or polyurethane, or other suitable material. Extension tubes 5 and 6 may be provided with clamps 21 and 22, respectively. Clamps 21, 22 are adapted to be movable from an open position to a substantially closed position to compress a corresponding extension tube 5, 6, and thereby inhibit fluid flow through the extension tube 5, 6. Catheter hub 8 may be releaseably connected to or integrally formed with the proximal end 18 of catheter main body 1. Similarly, extension tubes 5 and 6 may be releaseably connected to or integrally formed with the catheter hub 8.

Luer adapters 15 and 16 are integrally formed or otherwise associated with the ends of the extension tubes 5 and 6, respectively. Luer adapters 15 and 16 are adapted to be connected to a dialysis system at a time of dialysis, whereby the leer adapter 15 is fluidly coupled to the extension tube 5 and disposed in fluid communication with the perfusion lumen 2, and the luer adapter 16 is fluidly coupled to the extension tube 6 and disposed in fluid communication with the aspiration lumen 3.

Referring to FIG. 5, the catheter main body 1 defines an inflation port 44 disposed and configured to place the inflation lumen 4 in fluid communication with the inflatable balloon 38. During operation of the inflatable balloon 38, such as, for example, an inflation process to break-up or remove stenosis, fluid flow such as saline is supplied (not shown) via the inflation lumen 4 through the inflation-port 44 and into a chamber 36 of inflatable balloon 38.

FIGS. 7 and 8 show a distal portion 12 of the catheter assembly 10 of FIG. 1 including the inflatable balloon 38 during different stages of operation of the inflatable balloon 38. Inflatable balloon 38 may have any suitable length "L". Inflatable balloon 38 includes a first flange 37 disposed on the proximal end of the inflatable balloon 38, and a second flange 39 disposed on the distal end of the inflatable balloon 38. The first and second flanges 37, 39 are adapted to facilitate connection of the inflatable balloon 38 to the walls of the catheter main body 1. First and second flanges 37, 39 may be connected to the walls of the catheter main body 1 using any fastening technique including using an adhesive, sonic welding, or by any other suitable process. The connection of the inflatable balloon to the catheter main body 1 forms the chamber 36 for receiving the inflation fluid from inflation-port 44.

Inflatable balloon 38 may be disposed substantially adjacent to a proximal side of the side-ports 3a, 3b, and may surround any portion (e.g., distal portion 31 shown in FIG. 1) of the catheter main body 1. In other embodiments, the proximal half of the catheter main body 1 may be surrounded by the inflatable balloon 38, and in other embodiments any portion of the catheter main body may be surrounded by the inflatable balloon 38.

Inflatable balloon 38 according to various embodiments may be operated in conjunction with pharmacological intervention to prevent or reduce development of stenosis. Inflatable balloon 38 may be configured as a drug-eluting balloon for delivery of an anti-restenotic agent to an area of the vessel surrounding the catheter assembly 10 in which stenosis may develop. In some embodiments, the inflatable balloon 38 may be a tri-lumen percutaneous transluminal angioplasty (PTA) balloon that is coated with a base polymer layer including either a biostable polymer, such as phosphorylcholine, or a bioabsorbable polymer, such as, for example, polylactic acid (PLA), polyglycolic acid (PGA), poly-l-lactide (PLLA), their co-polymers, (e.g., PGA/PLA), etc. In some embodiments, the polymer layer may be impregnated with an anti-restenotic agent, such as, for example, paclitaxel, sirolimus, biolimus, tacrolimus, picrolimus, or any other—limus family member drug. In some embodiments, the polymer and drug elution characteristics may be designed so that complete elution of the drug occurs over about a 28-day time period. Inflatable balloon 38 may additionally, or alternatively, be configured as a "weeping balloon" with pores that open at relatively high pressures, such as greater than 8 atmospheres.

In an alternative embodiment not shown, the catheter main body 1 may include a plurality of inflation lumens 4 adapted to allow the inflatable balloon 38 to substantially evenly inflate around the circumference of the catheter main body 1. In such alternative embodiments, the catheter main body 1 may include multiple inflation-ports 44 adapted to place the inflation lumen 4, or plurality of inflation lumens 4, of the catheter main body 1 into fluid communication with the inflatable balloon 38.

Referring to FIG. 8, the inflatable balloon 38 may be configured to permit expansion thereof in the distal direction (e.g., along the longitudinal axis "A-A") to enable at least a distal portion of the inflatable balloon 38 to extend over at least a proximal portion of the side-ports 3a, 3b during inflation of the inflatable balloon 38. The expansion of the inflatable balloon 38 in the distal direction may act to dislodge and/or move material, such as thromboembolic material, away from, or into, the side-ports 3a, 3b. If material is pushed into the side-ports, fluid flow and/or heparin can then be used to clear the side-ports 3a, 3b by pressure or chemical reaction. In other embodiments, the inflatable balloon 38 may not extend over the side-ports 3a, 3b, but rather expand to break up any tissue that has attached to the catheter main body 1, such as thrombus or fibrin sheath.

Turning now to FIGS. 2 and 9 through 16, an embodiment of a catheter assembly 100 is shown including an elongated catheter main body 11 and the inflatable balloon 38 of FIG. 1 disposed around a distal portion 131 of the catheter main body 11. Catheter main body 11 may include one or more lumens. The catheter main body 11 includes a proximal end 118 and a distal end 119.

Catheter main body 11 includes an internal septum 99 (FIG. 9) extending along the length thereof. Septum 99 and the walls of the catheter main body 11 form a perfusion lumen 102 and an aspiration lumen 103. Septum 99 is located such that the aspiration lumen 103 has a larger cross-sectional area than the cross-sectional area of the perfusion lumen 102. Septum 99 of the catheter main body 11 of FIG. 9 is similar to the septum 9 of the catheter main body 1 shown in FIG. 3

(except for its location) and further description thereof is omitted in the interests of brevity.

Figure 14:
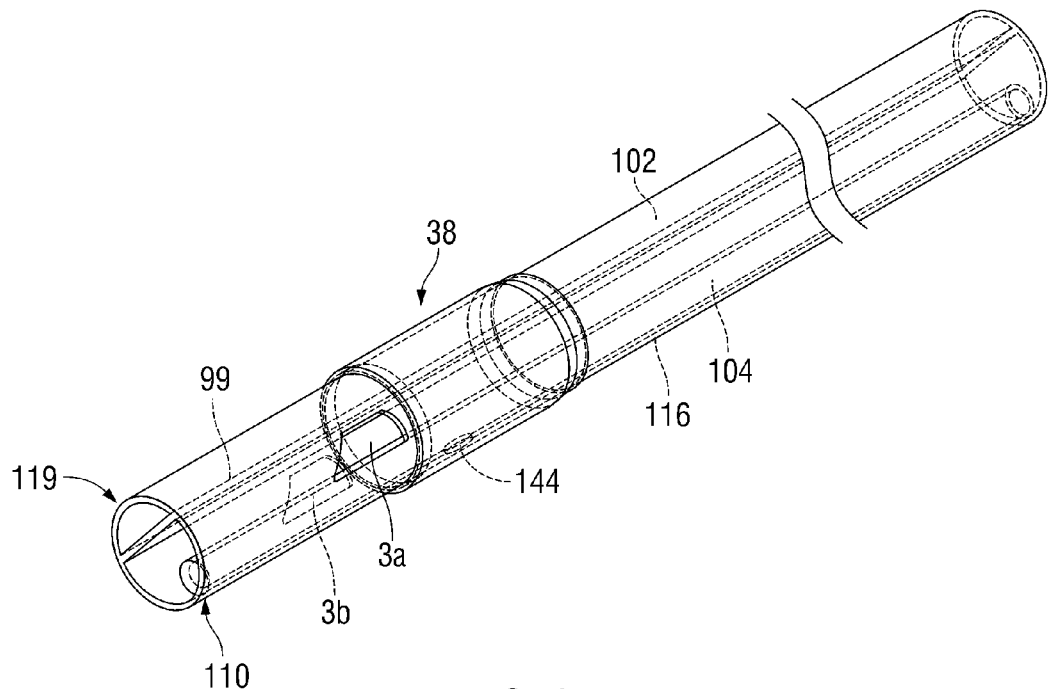
FIG. 14 is a partial, perspective view similar to FIG. 13, showing another embodiment of the catheter main body.

Catheter assembly 100 includes an inflation lumen 104 disposed within the catheter main body 11. The inflation lumen 104 may have any suitable dimensions, such as diameter and length. In some embodiments, the length of the inflation lumen 104 may be different than the length of the perfusion lumen 102 and the aspiration lumen 103. In some embodiments, such as shown in FIG. 14, the perfusion lumen 102, the aspiration lumen 103, and the inflation lumen 104 may have substantially the same length. In the embodiment shown in FIG. 14, the distal end of the inflation lumen 104 would be sealed at the distal end to enable the inflation fluid to exert pressure into the inflatable balloon 38.

Referring to FIG. 10, the inflation lumen 104 is coupled to or otherwise associated with the aspiration-lumen wall portion 14. Catheter main body 11 defines an inflation-port 144 disposed and configured to place the inflation lumen 104 in fluid communication with the inflatable balloon 38.

Figure 13:
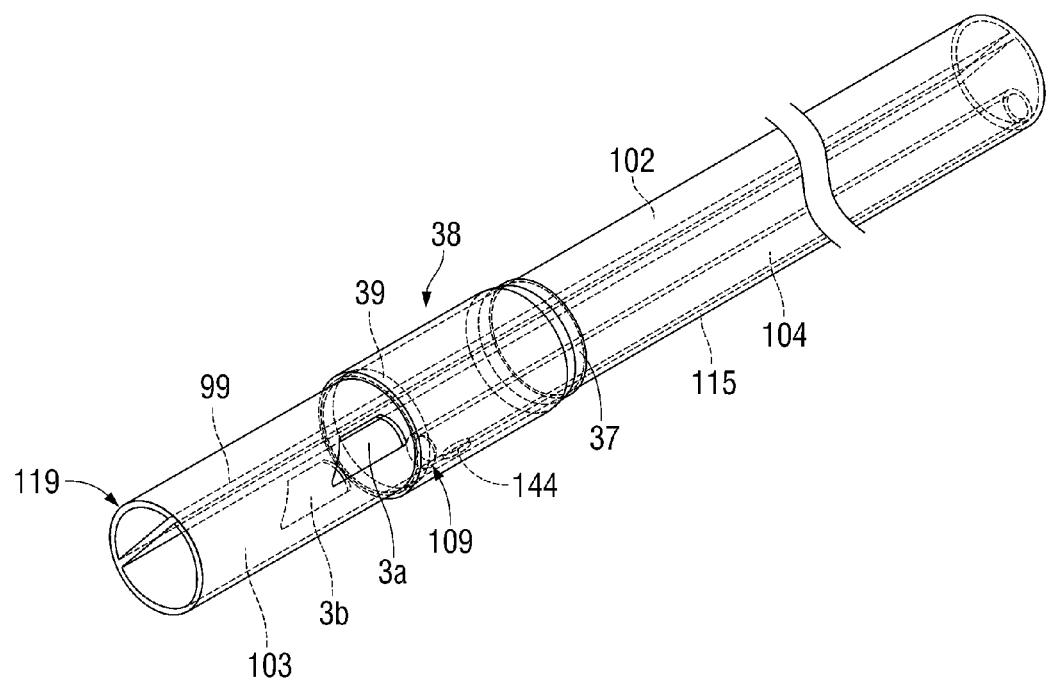
FIG. 13 is a partial, perspective view of the catheter main body of the catheter assembly of FIG. 2.

Referring to FIG. 13, the inflation lumen 104 includes a distal end 109. As cooperatively shown in FIGS. 2 and 13, the distal end 109 is disposed within the distal portion 131 (FIG. 2) of the catheter main body 11 surrounded by the inflatable balloon 38. As best shown in FIGS. 15 and 16, the inflation lumen 104 is provided with an end cap 107 adapted to fluidly seal the distal end 109 of the inflation lumen 104. In this configuration, fluid flow (e.g., saline, etc.) supplied via the inflation lumen 104 can be wholly used to operate the inflatable balloon 38, which may allow for user-control of operational characteristics of the inflatable balloon 38, such as, for example, rate of inflation, inflation volume, and pressure exerted by the inflatable balloon 38 on the vessel surrounding the catheter main body 11.

Figure 2:
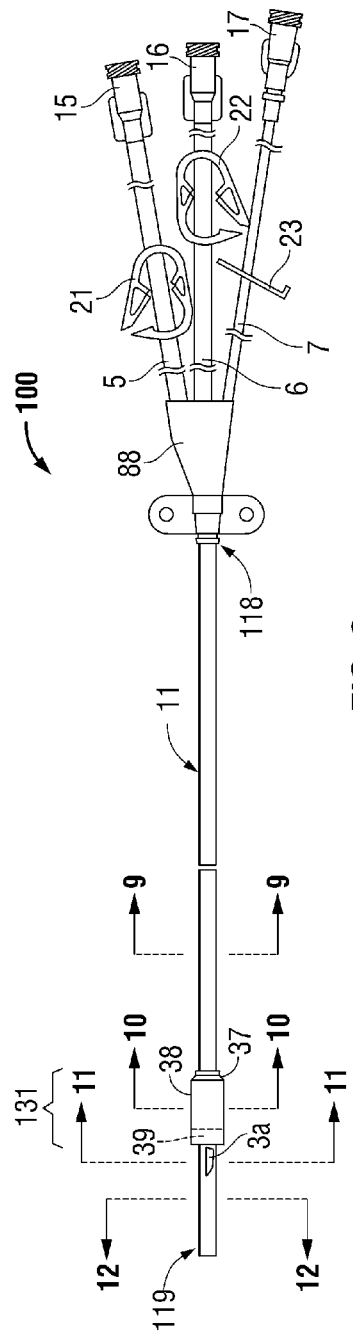
FIG. 2 is a top view of another embodiment of a catheter assembly including an inflatable balloon in accordance with the present disclosure.

To facilitate connection of the catheter assembly 100 to a medical device, such as a dialyzer, an injection syringe, or other apparatus, a catheter hub 88 of the catheter assembly 100 is provided with extension tubes 5, 6 and 7. Catheter hub 88 may be releaseably connected to or integrally formed with the proximal end 118 of catheter main body 11. Luer adapters 15, 16 and 17 are integrally formed or otherwise associated with the ends of the extension tubes 5, 6 and 7, respectively. Extension tube 7 may be provided with a clamp 23 (FIG. 2). Luer adapters 15 and 16 are adapted to be connected to a dialysis system at a time of dialysis, whereby the luer adapter 15 is fluidly coupled to the extension tube 5 and disposed in fluid communication with the perfusion lumen 102, the fuer adapter 16 is fluidly coupled to the extension tube 6 and disposed in fluid communication with the aspiration lumen 103. The luer adapter 17 is fluidly coupled to the extension tube 7 and disposed in fluid communication with the inflation lumen 104. Further description of the extension tubes 5 and 6 of the catheter assembly 100 and other structures, such as clamps 21 and 22, in common with the catheter assembly 10 shown in FIG. 1 is omitted in the interests of brevity.

In either embodiment, inflating the inflatable balloon will enable the break-up and/or dislodging of any tissue, such as stenosis, thrombus or fibrin sheath, that may have adhered to the catheter main body 1. Further, inflating the inflatable balloon will compress any stenosis found on the vessel wall away from the catheter, thereby helping to keep the blood vessel around the catheter patent. Also, if a drug eluting balloon is utilized, or the balloon is coated with an anti-stenotic or anti-thrombogenic material, as described above, the formation of further stenosis or thrombus may be slowed or eliminated, further helping to maintain blood flow around the catheter. The inflatable balloon may be inflated at any time, including before a dialysis session or in between dialysis sessions, to help maintain the patency of the catheter.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of dislodging tissue from a catheter, the method comprising:
   providing a dialysis catheter comprising
      an elongated main body defining a longitudinal axis and having a length along the longitudinal axis between a distal end and a proximal end, the elongated main body defining at least one internal lumen,
      a side-port in fluid communication with the at least one internal lumen, and
      an inflatable balloon disposed adjacent to the side-port on an outer surface of the elongated main body and configured to move from a deflated state to an inflated state; and
   inflating the inflatable balloon to dislodge tissue from the elongated main body by expanding the inflatable balloon in a distal direction so that at least a distal portion of the inflatable balloon extends over at least a proximal portion of the side-port and moves material away from, or into, the side port as the inflatable balloon expands in the distal direction.

2. The method of claim 1 wherein the inflatable balloon is disposed adjacent the distal end of the elongated main body.

3. The method of claim 1 wherein the inflatable balloon is coated with a base polymer layer.

4. The method of claim 1 further comprising the step of inflating the inflatable balloon evenly around the elongated main body of the dialysis catheter.

5. The method of claim 1 wherein the dialysis catheter further comprises a plurality of side-ports in fluid communication with a plurality of internal lumens.

6. The method of claim 1 further comprising the step of providing heparin to the side-port to clear the side-port by chemical reaction.

7. The method of claim 1 further comprising providing an end cap adapted to fluidly seal the at least one internal lumen.

8. The method of claim 1 further comprising the step of sealing a distal end of the at least one internal lumen to enable inflation fluid to exert pressure into the inflatable balloon.

9. The method of claim 1 further comprising the step of supplying saline to the inflatable balloon.

10. The method of claim 1 further comprising the step of connecting the dialysis catheter to a medical device.

11. The method of claim 1 wherein the inflatable balloon is a drug eluting balloon.

12. The method of claim 11 wherein the drug eluting balloon elutes an anti-restenotic agent.

13. The method of claim 1 wherein the inflatable balloon includes pores.

14. The method of claim 13 further comprising the step of providing a pressure greater than 8 atmospheres to the inflatable balloon to open the pores.

15. The method of claim 1 wherein the inflatable balloon is configured to extend at least partially over the side-port when in the inflated state.

16. The method of claim 15 further comprising:
   deflating the inflatable balloon; and flowing fluid through the internal lumen and out the side-port to remove any tissue dislodged by the inflatable balloon into the side-port.

\* \* \* \* \*